United States Patent [19]

Duinker et al.

[11] Patent Number: 4,844,908

[45] Date of Patent: Jul. 4, 1989

[54] METHOD OF PREPARING TABLETS WITH CLOVOXAMINE FUMARATE AND TABLETS THUS PREPARED

[75] Inventors: Hendrik Duinker; Hugo Bijl, both of Olst, Netherlands

[73] Assignee: Duphar International Research B.V., Weesp, Netherlands

[21] Appl. No.: 124,045

[22] Filed: Nov. 23, 1987

[30] Foreign Application Priority Data

Nov. 27, 1986 [NL] Netherlands ......................... 8603004

[51] Int. Cl.$^4$ ........................... A61K 9/28; A61K 9/22
[52] U.S. Cl. .................................... 424/474; 424/468; 424/470; 424/493; 424/497; 424/498
[58] Field of Search ............... 424/470, 468, 474, 475, 424/493, 497, 498

[56] References Cited

U.S. PATENT DOCUMENTS

| | | | |
|---|---|---|---|
| 3,340,152 | 9/1967 | Hotko | 424/470 X |
| 4,086,361 | 4/1978 | Welle et al. | 514/640 X |
| 4,756,911 | 7/1988 | Drost et al. | 424/470 X |

FOREIGN PATENT DOCUMENTS

| | | | |
|---|---|---|---|
| 2554717 | 5/1985 | France | 424/470 |
| 58-109414 | 6/1983 | Japan | 424/470 |

Primary Examiner—Thurman K. Page
Attorney, Agent, or Firm—Stevens, Davis, Miller & Mosher

[57] ABSTRACT

Clovoxamine, i.e., 4'-chloro-5-methoxyvalerophenone-O-(2-aminoethyl)oxime is a known compound having antidepressive activity. The fumarate (1:1) of clovoxamine may be administered orally in the form of tablets.

5 Claims, No Drawings

METHOD OF PREPARING TABLETS WITH CLOVOXAMINE FUMARATE AND TABLETS THUS PREPARED

Clovoxamine, i.e. 4'-chloro-5-methoxyvalerophenone-0-(2-aminoethyl)oxime is a known compound having antidepressive activity. The fumarate (1:1) of clovoxamine may be administered orally in the form of tablets.

Pharmacologically active compounds which are administered orally in the form of tablets are usually processed to tablets by homogenously mixing the active substance as such or in the form of a suitable acid addition salt with the conventional carrier materials and auxiliary substances (so-called dry-mix method), granulating the resulting mixture and compressing tablets from the granulate after the addition of lubricants. The tablets thus obtained often are additionally provided with a coating layer.

After many investigations in which numerous possibilities have been investigated it has been found that from clovoxamine fumarate in this manner tablets cannot be obtained the properties of which, for example, tablet hardness, abrasion resistance, disintegration time and dissolution rate of the active substance from the tablets, have the required values.

When the composition of the tablet cores was varied, improvement of the breaking strength and/or abrasion resistance was associated with an unacceptable deterioration of the disintegration time and/or the dissolving rate of the active substance.

It has been found that tablet cores which comprise clovoxamine fumarate as the active substance and which satisfy the values for tablet hardness, abrasion resistance, disintegration time and dissolution rate of the active substance to be imposed on qualitatively good tablets, can be obtained by dissolving the active substance clovoxamine fumarate, while heating, in a mixture of 25-75% of an alcohol having 1-4 C-atoms and 75-25% of water and mixing this solution with the conventional carrier materials, granulating this mixture and drying it, and compressing it into tablet after mixing with the conventional lubricants. The tablets to be obtained in this manenr may be provided with a coating layer in a manner known per se.

In this manner tablets are obtained which satisfy the following specifications:
(a) tablet hardness $\geq 60$ N.
(b) abrasion resistance: no abrasion or other damage, for example, capping/laminating.
(c) disintegration time: $\leq 15$ minutes.
(d) dissolution rate of the active substance (in water): 70% within 60 minutes (USP paddle method, 50 rmp).

Tablets of an excellent quality are obtained as follows:
Clovoxamine fumarate solution:25%
Maize starch:16%
Mannitol:31.4%
Secondary calcium hydrogen phosphate:20%
Polyvinyl pyrrolidone:5%

The above dry components are thoroughly mixed and wetted with the clovoxamine fumarate solution and the resulting mixture is granulated and dried. The granulate thus obtained is mixed with:
Sodium stearyl fumarate:1.5%
Silicon dioxide (Aerosil):0.1%
Crospovidone:1.0%
as lubricants and then compressed to tablets in a conventional manner.

The 25% clovoxamine fumarate solution used preferably consists of 55% of clovoxamine fumarate, 27% of water and 18% of ethanol, i.e. of a solution of clovoxamine fumarate in a mixture of 60% of water and 40% of ethanol.

It is extraordinarily surprising that clovoxamine fumarate is readily soluble in mixtures of 25-75% of an alcohol having 1-4 C-atoms and 75-25% of water, since it is substantially insoluble to poorly soluble in water, methanol, ethanol, isopropanol, chloroform, diethylether, cyclohexanone, hexane, tetrahydrofuran and methylethyl ketone.

We claim:

1. A method of preparing pharmaceutical tablets for oral administration by mixing a solution of the active substance with the conventional carrier materials, granulating and drying this mixture, and after the addition of lubricants, compressing it to tablets, characterized in that the active substance clovoxamine fumarate (1:1) is dissolved in a mixture of 25-75% of an alcohol having 1-4 C-atoms and 75-25% of water, which solution is mixed with the remaining components for granulating.

2. A method as claimed in claim 1, characterized in that clovoxamine fumarate is dissolved in a mixture of 40% of ethanol and 60% of water.

3. Tablets obtained according to the method as claimed in claim 1 or 2.

4. The method of claim 1 whereas the tablets are provided with a coating layer.

5. Tablets obtained according to the method as claimed in claim 4.

* * * * *